United States Patent [19]

Gruber et al.

[11] 4,081,465

[45] Mar. 28, 1978

[54] METHOD FOR THE OXIDATIVE DEHYDROGENATION OF ISOBUTYRIC ACID

[75] Inventors: Wilhelm Gruber, Darmstadt; Guenter Schroeder, Ober-Ramstadt, both of Germany

[73] Assignee: Rohm GmbH, Darmstadt, Germany

[21] Appl. No.: 733,326

[22] Filed: Oct. 18, 1976

[30] Foreign Application Priority Data

Nov. 13, 1975 Germany .............................. 2550979

[51] Int. Cl.$^2$ ............................................ C07C 51/24
[52] U.S. Cl. ................................................ 260/526 N
[58] Field of Search ................................... 260/526 N

[56] References Cited

U.S. PATENT DOCUMENTS

| 3,207,806 | 9/1965 | Bajars | 260/526 N |
| 3,917,673 | 11/1975 | Watkins | 260/526 N |

FOREIGN PATENT DOCUMENTS

721,773   11/1965   Canada ............................ 260/526 N

*Primary Examiner*—Vivian Garner
*Attorney, Agent, or Firm*—Curtis, Morris & Safford

[57] ABSTRACT

In a method for the oxidative dehydrogenation of isobutyric acid in the gas phase, in the presence of oxygen and water vapor at a temperature from 300° C. – 500° C., and in the presence of a solid catalyst, the improvement wherein said catalyst initially consists essentially of at least one member selected from the group consisting of elemental molybdenum, elemental tungsten, molybdenum trioxide, and tungsten trioxide.

3 Claims, No Drawings

METHOD FOR THE OXIDATIVE DEHYDROGENATION OF ISOBUTYRIC ACID

The present invention relates to the catalytic oxidative dehydrogenation of isobutyric acid to methacrylic acid.

A number of methods are known by which hydrogen can be cleaved from derivatives of isobutyric acid, or from this acid itself, whereby the corresponding derivatives of methacrylic acid, or this acid itself, are formed. These processes differ principally in the catalyst used therein. For the oxidative dehydrogenation of isobutyronitrile or isobutyric acid esters, catalysts have already been used which contain the elements molybdenum or tungsten in compounds with other elements such as selenium, tellurium, or antimony. However, these catalysts are not suitable for the oxidative dehydrogenation of free isobutyric acid. For this reaction, catalysts having as the active component a phosphate of bismuth, iron, or of lead have proved particularly advantageous.

According to German Patent Publication DOS 21 18 904, methacrylic acid is obtained from isobutyric acid using a bismuth-iron-lead-phosphate contact, in the presence of oxygen and water vapor, in a yield of 73.1% of the isobutyric acid employed. The selectivity is, for example, 85%. The space-time-yield, i.e. the achievable yield per unit time using a defined unit volume of the contact, in this process has a value of about 250 grams/-liter/hour and is quite low. Therefor, for amounts of product on a large industrial scale, a very large reactor volume and a large amount of the contact are needed.

The contact employed is relatively expensive which is caused, on the one hand, by the content of the expensive element bismuth, and, on the other hand, because of the complicated composition, which requires considerable care in the preparation of the catalyst. The durability of the contact is relatively short and its sensitivity to deviations from the optimum operating conditions is large. For the aforementioned reasons, the contact mentioned above is too expensive for a technical process, despite good yields and selectivity.

The contact described in German Patent Publication DOS 24 50 878 for the same reaction, which contact contains no bismuth and contains iron-lead-phosphate as the active component, is, to be sure, considerably less expensive and permits space-time-yields of 400 to 500 grams/liter/hour. However, its lifetime is undesirably low in view of the still relatively low space-time-yield in this case.

Contacts of the same type are also described in German Patent Publication DOS 24 38 464. They have the disadvantages described above.

Contacts have now been found which permit a considerable increase in the space-time-yield and make a high durability possible. They contain molybdenum oxide or tungsten oxide or mixtures thereof, as the active component. Because of this simple composition, they are easily preparable and insensitive. Because of the high space-time-yield, a relatively small amount of the contact is necessary, whereby the costs for renewal of the contact are substantially reduced.

Thus, the object of the invention is a process for the oxidative dehydrogenation of isobutyric acid to methacrylic acid in the presence of oxygen and water vapor in the gas phase on a solid catalyst at temperatures of 300° C. – 500° C., whereby, according to the invention, the catalyst essentially comprises molybdenum and/or tungsten, or their oxides, and optionally additionally comprises an inert carrier material. The composition of the active catalyst under the reaction conditions is not known. Active catalysts can be formed as well from elemental molybdenum or tungsten as well as from the trioxides of these metals. Since the reaction gas, because of its content of oxygen, water vapor, organic substances, and usually some carbon monoxide, can act both oxidatively as well as reductively, it can be assumed that the active catalyst contains oxidic compounds of tungsten and/or of molybdenum in different valence states (cf. also Gmelin, Vol. 53–55, 8th ed., 1935).

Operating temperatures of 300° C. – 400° C. are most advantageous. The isobutyric acid is evaporated and led over the contact together with oxygen and water vapor. The oxygen content is, for example, between 0.5 and 1 mole, preferably between 0.6 and 0.8 mole, per mole of isobutyric acid. Water vapor can be introduced in an amount which is about tenfold the molar amount of isobutyric acid introduced. It is advantageous to dilute the reaction gas with an inert gas, particularly nitrogen, so that one mole of isobutyric acid is contained in about 300–600 liters, and preferably in about 350–500 liters, of the reaction gas. The oxygen/nitrogen ratio in the reaction gas is, as a rule, lower than in atmospheric air, so that it is advantageous to recycle the reaction gas and from time to time to introduce sufficient atmospheric air to reach the desired oxygen content.

The contact is suitably introduced as a granular bulk material into a tube-bundle reactor. Although molybdenum oxide or tungsten oxide can be employed alone, the use of an inert carrier material is more economic. As carriers, kieselguhr or silica gel are suitable. A carrier material is to be viewed as inert, if, without a content of molybdenum oxide or tungsten oxide, it induces no reaction, under the reaction conditions, of the isobutyric acid introduced or, in any case, does not bring about an uncontrolled oxidative or purely thermal decomposition. The contacts according to the invention contain no active elements other than molybdenum and tungsten. Nevertheless, technical products which contain small amounts of compounds of other elements as impurities can be used. Compounds of other metals should only be present in the contacts if they can be viewed as inert in the sense of the invention or if the amount of such materials is so small that they do not influence the catalytic reaction.

The contacts of the invention, bound to a carrier, can be prepared by known methods, for example, by soaking the porous inert carrier material with an aqueous solution of ammonium molybdate, ammonium tungstate or similar soluble salts of these elements which, on heating, decompose to the corresponding oxide, drying and heating to temperatures from 500° C. to 700° C. One can also proceed from elemental molybdenum and/or tungsten which, for example, is finely divided on an inert carrier.

The best results are obtained with contacts containing mixtures of the elements molybdenum and tungsten, or their acids. The mixing ratio is, for example, between 90:10 and 10:90, calculated as parts by weight of the elements molybdenum and tungsten. The process of the invention permits the achievement of space-time-yields up to more than 1000 grams/liter/hour.

The methacrylic acid is obtained from the reaction gas stream, just as in the known processes described earlier herein, by condensation or solvent extraction.

A better understanding of the present invention and of its many advantages will be had by referring to the following specific Examples, given by way of illustration.

In the Examples, an externally-heatable contact tube having a 20 mm inner diameter is filled with 25 ml of contact granules. A gas mixture is prepared from evaporated isobutyric acid (IBA), oxygen, water vapor and nitrogen, and is passed over the contact. (In each case, the gas batch contains one mole of isobutyric acid.) The reaction gases leaving the reactor are cooled and condensed.

The yield and selectivity of the methacrylic acid (MA) formed are determined gas chromatographically and by determination of the acid number in the liquid reaction mixture so obtained.

The reaction conditions and the results are collated in the following Table:

TABLE

| Ex. No. | Composition of Catalyst as Introduced (Ratios by weight) | $O_2$/IBA (mole/mole) | $H_2O$ (moles) | $N_2$ (liters) | Temp- (° C.) | Time (min.) | MA-Selectivity (%) | Space-Time Yield (g/l/h) |
|---|---|---|---|---|---|---|---|---|
| 1 | $WO_3$/$MoO_3$ 40% on kieselguhr (W:Mo = 87:13) | 0.6 | 10 | 150 | 400 | 67 | 69.5 | 830 |
| 2 | W/Mo 50% on kieselguhr (W:Mo = 50:50) | 0.8 | 10 | 150 | 350 | 58 | 55 | 969 |
| 3 | W/Mo 50% on kieselguhr (W:Mo = 50:50) | 0.75 | 10 | 110 | 350 | 48 | 73.5 | 1030 |
| 4 | $WO_3$ 35% on $Al_2O_3$—$SiO_2$ | 0.8 | 10 | 150 | 450 | 66 | 89 | 752 |
| 5 | Mo 40% on $SiO_2$ | 0.5 | 8 | 130 | 430 | 50 | 72.5 | 675 |

What is claimed is:

1. In a method for the oxidative dehydrogenation of isobutyric acid in the gas phase, in the presence of oxygen and water vapor at a temperature from 300° C. – 500° C., and in the presence of a solid catalyst, the improvement wherein said catalyst consists essentially of at least one member selected from the group consisting of elemental molybdenum, elemental tungsten, molybdenum trioxide, and tungsten trioxide.

2. A method as in claim 1 wherein said catalyst is present on an inert carrier.

3. A method as in claim 1 wherein molybdenum and tungsten are present in said catalyst in a weight ratio from 90:10 to 10:90.

* * * * *